(12) United States Patent
LaBrosse et al.

(10) Patent No.: US 8,182,914 B2
(45) Date of Patent: *May 22, 2012

(54) WATER CONTACT INDICATOR

(75) Inventors: Paul R. LaBrosse, Forest Lake, MN (US); Russell D. Birkholz, Maplewood, MN (US); Mark E. Schwartz, Maplewood, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 162 days.

This patent is subject to a terminal disclaimer.

(21) Appl. No.: 12/752,314

(22) Filed: Apr. 1, 2010

(65) Prior Publication Data

US 2010/0186659 A1    Jul. 29, 2010

Related U.S. Application Data

(62) Division of application No. 10/987,897, filed on Nov. 11, 2004, now Pat. No. 7,732,046.

(60) Provisional application No. 60/519,970, filed on Nov. 14, 2003.

(51) Int. Cl.
*B32B 7/12* (2006.01)
*B32B 15/04* (2006.01)

(52) U.S. Cl. ............... 428/343; 428/354; 428/355 R; 428/480; 428/537.5; 428/500

(58) Field of Classification Search .......... 428/343, 428/354, 355 R, 480, 537.5, 500
See application file for complete search history.

(56) References Cited

U.S. PATENT DOCUMENTS

| RE24,906 E | 12/1960 | Ulrich |
|---|---|---|
| 3,844,718 A | 10/1974 | Cohen |
| 4,557,205 A | 12/1985 | Strobel et al. |
| 4,743,238 A | 5/1988 | Colon et al. |
| 5,238,623 A | 8/1993 | Mrozinski |
| 5,389,426 A | 2/1995 | Arens et al. |
| 5,518,763 A | 5/1996 | Patnode et al. |
| 5,660,925 A | 8/1997 | Cooley et al. |
| 5,747,146 A | 5/1998 | Kashiwazaki et al. |
| 5,862,101 A | 1/1999 | Haas et al. |
| 5,948,546 A | 9/1999 | Bafford et al. |
| 6,117,530 A | 9/2000 | Jonza et al. |
| 6,492,005 B1 | 12/2002 | Ohbayashi et al. |
| 7,105,225 B2 | 9/2006 | Birkholz et al. |
| 7,732,046 B2 * | 6/2010 | LaBrosse et al. ............ 428/343 |
| 2003/0096107 A1 | 5/2003 | Birkholz et al. |
| 2006/0263597 A1 | 11/2006 | Birkholz et al. |

FOREIGN PATENT DOCUMENTS

| EP | 1 001 264 A1 | 5/2000 |
|---|---|---|
| EP | 1 043 377 A2 | 10/2000 |
| JP | 61-250535 | 4/1985 |
| JP | 06-202560 | 7/1994 |
| JP | 07-098279 | 4/1995 |
| JP | 07-098309 | 4/1995 |

(Continued)

*Primary Examiner* — Betelhem Shewareged
(74) *Attorney, Agent, or Firm* — Stephen F. Wolf

(57) ABSTRACT

The present invention discloses an adhesive article. The adhesive article comprises a first layer comprising a fluid transport substrate, comprising a low molecular weight hydrophilic polymer resin, the first layer having a first major surface and a second major surface. The adhesive article additionally comprises a second layer comprising a fluid transportable ink, the second layer being associated with the second major surface of the second layer. The adhesive article also comprises an adhesive layer.

15 Claims, 2 Drawing Sheets

FOREIGN PATENT DOCUMENTS

| | | |
|---|---|---|
| JP | 07-140078 | 6/1995 |
| JP | 08-254953 | 1/1996 |
| JP | 09-325698 | 12/1997 |
| JP | H10-90244 | 4/1998 |
| JP | 10-254360 | 9/1998 |
| JP | 2000-106596 | 4/2000 |
| JP | 2000-122546 A | 4/2000 |
| JP | 2000-151776 A | 5/2000 |
| JP | 3058634 | 7/2000 |
| JP | 2001-051600 | 2/2001 |
| JP | 2002-311837 | 10/2002 |
| WO | WO 98/23920 | 6/1998 |
| WO | WO 02/43965 A2 | 6/2002 |
| WO | WO 03/031531 A1 | 4/2003 |

* cited by examiner

WATER CONTACT INDICATOR

RELATED APPLICATIONS

This application is a divisional application of U.S. Ser. No. 10/987,897, now allowed, filed Nov. 11, 2004, now U.S. Pat. No. 7,732,046 which claims the benefit of priority of provisional application U.S. Ser. No. 60/519,970, filed Nov. 14, 2003 both of which are herein incorporated by reference.

FIELD OF THE INVENTION

The present invention relates to adhesive articles having the capability to detect fluid, especially water, exposure.

BACKGROUND OF THE INVENTION

An adhesive article, for example a tape or a label that indicates fluid exposure is desirable for many uses. For example, such an adhesive article may help detect minor leaks in water tight pipes. Additionally, these adhesive articles may be useful for detecting water exposure of electronics, especially hand-held electronics. For example, an adhesive article that indicates water exposure would be useful for manufacturers of electronic devices, for example cellular phones, personal digital assistants, hand held computers, battery chargers, or small electric appliances, to help determine functional failure. The adhesive article may be placed on the electronic device, either within the electronic portion of the device or on an external casing. If the device had been immersed or a sensitive component contacted with a fluid, such as water, the warranty could be voided or the cause of failure determined.

Some adhesive articles used for fluid indication describe a layer of ink on a substrate. The ink is displayed in a pattern that is altered upon exposure to water. For example, the ink may be in stripes or dots, which blur upon exposure to water. Some additional adhesive articles have a transparent cover film to prevent smudging of the ink prior to water exposure. Other adhesive articles utilize an ink that changes color upon the exposure to water.

SUMMARY OF THE INVENTION

Some commercially available adhesive articles indicate too easily under high humidity conditions. Some additional commercially available adhesive articles may not indicate water contact at all after exposure to high humidity conditions. What is desired is a water indicating adhesive article that will indicate upon sustained water exposure, but does not indicate in a high humidity environment.

The present invention discloses an adhesive article. The adhesive article comprises a first layer comprising a fluid transport substrate, comprising a low molecular weight hydrophilic polymer resin, the first layer having a first major surface and a second major surface. The adhesive article additionally comprises a second layer comprising a fluid transportable ink, the second layer being associated with the second major surface of the second layer. The adhesive article also comprises an adhesive layer.

DETAILED DESCRIPTION OF THE INVENTION

Figure 1:
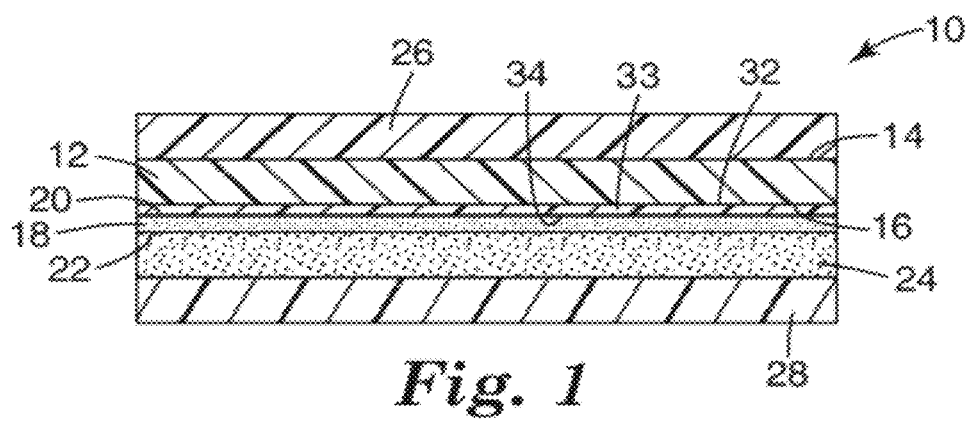
FIG. 1 is a cross-sectional view of a first embodiment of the invention.

An embodiment of the fluid indicating adhesive article is illustrated in FIG. 1. The adhesive article 10 comprises a fluid transport substrate. The fluid transport substrate is a multilayer structure comprising a porous layer 12 and a low molecular weight hydrophilic polymer resin layer 33. Porous layer 12 has a first major surface 14 and a second major surface 16. Resin layer 33 has a first major surface 32 and a second major surface 34. The first major surface 32 of the resin layer 22 in associated with the second major surface 16 of the porous layer 12. For the purpose of the present application, the term associated means on the same side as a defined surface, and in contact, whether directly or by other layers, with that surface. A fluid transportable ink layer 18 is coated onto the second major surface 34 of the resin layer 33. The ink layer has a first major surface 20 and a second major surface 22. The first major surface 20 of the ink layer 18 is in contact with the second major surface 34 of the resin layer 33. The adhesive article 10 additionally comprises an adhesive layer 24 applied onto the second major surface 22 of the ink layer 18.

The adhesive article 10 additionally comprises a transparent layer 26 laminated onto the first major surface 14 of the substrate 12. The adhesive article 10 also comprises a release liner 28 set on the adhesive layer 24 opposite the second major surface 22 of the ink layer 18.

Figure 2:
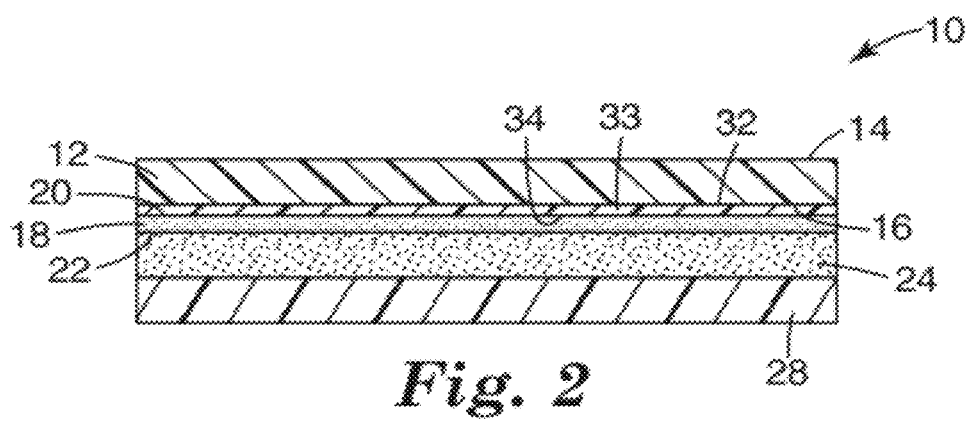
FIG. 2 is a cross-sectional view of a second embodiment of the invention.

Another embodiment of the invention is illustrated in FIG. 2. FIG. 2 is the same embodiment as shown in FIG. 1 with the exception that the transparent layer 26 has been removed.

Substrate

The fluid indicating adhesive article of the present invention includes a substrate capable of fluid transport ("fluid transport substrate".) A fluid transport substrate will transport fluid through the substrate. For example, the substrate may comprise a microporous film as described in U.S. Pat. No. 5,238,623 to Mrozinski, which is incorporated by reference. Generally, the fluid transport substrate comprises a porous layer. In many embodiments, the fluid transport substrate comprises a fibrous substrate. The fibrous substrate is generally capable of absorbing a fluid. However, the fibrous substrate generally will not saturate in a high humidity environment. In certain embodiments, the substrate is a water absorbent substrate. The water absorbent substrate is generally made of a material that maintains a cohesive form when wet. Suitable substrates include paper, such as cellulose based paper, for example paper towels and copy grade paper.

Additionally, woven and nonwoven fabrics and polyolefins may be suitable substrates. Polyolefins may be treated to enhance fluid absorbance, for example by treating with a hydrophilic coating or blending the polyolefin with a hydrophilic fiber. However, any coating used to make the polyolefin hydrophilic should be chosen so it will not interfere with, or react negatively to the adhesive chosen. Melt-blown or spun-bond techniques can be employed to make such nonwoven webs. Nonwoven webs can also be prepared, for example, on a RANDO WEBBER (Rando Corporation, Macedon, N.Y.) air-laying machine or on a carding machine.

Representative examples polyolefins include, for example, polypropylene, polyethylene, high density polyethylene, low density polyethylene, linear low density polyethylene, and linear ultra low density polyethylene, and polybutylenes. Additional materials that may be useful for the substrate of the present invention include nylon, polyester (e.g., polyethylene terephthalate), vinyl copolymers, such as polyvinyl chlorides, both plasticized and unplasticized, and polyvinyl acetates; olefinic copolymers, such as ethylene/methacrylate copolymers, ethylene/vinyl acetate copolymers, acrylonitrile-butadiene-styrene copolymers, and ethylene/propylene copolymers; acrylic polymers and copolymers; polycaprolactones; and combinations of the foregoing. Mixtures or blends of any plastic or plastic and elastomeric materials such as polypropylene/polyethylene, polyurethane/polyolefin, polyurethane/polycarbonate, polyurethane/polyester, can also be used.

Specific examples of suitable substrates include a cellulose paper, such as those sold under the trade designations Ultrasorb FP "matte," absorbent cellulose paper and GW FORM Bond paper, both commercially available from MeadWestvaco Corp. of Wickliffe, Ky. The substrate may also be a standard weight copy paper, such as paper sold under the tradename COPYPLUS Standard White, available from International Paper, Memphis, Tenn.

The fluid transport substrate may be a single layer or a multiple layer construction comprising one or more of the absorbent materials described above. Embodiments of a multilayer fluid transport substrate may also include an additional layer or layers to control the colorfastness, humidity fastness and/or migration of the ink through the fluid transport layer. Such layers may include hydrophilic resins, for example, polyethyloxazoline, vinyl polymers such as polyvinyl-alcohol (PVA) or polyvinyl-pyrrolidone (PVP), vinyl-pyrrolidone-vinyl acetate copolymer, or combinations thereof.

A multilayer embodiment of the fluid transport substrate of the present invention may be formed by any conventional techniques, such as coating, laminating or coextrusion. Additional embodiments include adding a hydrophilic resin as an additive incorporated into a porous layer.

In embodiments having a hydrophilic resin, the choice of hydrophilic polymer resin ensures that the resin has appropriate water solubility to allow migration of the ink layer through the fluid transport substrate while providing an adequate migration barrier under high humidity conditions. Generally, low molecular weight is a predictor of solubility of a polymer. Lower molecular weight polymers include molecular weights of less than 500,000. In some embodiments, the lower molecular weight polymers include molecular weights of less than or equal to 10,000.

In many embodiments, the fluid transport substrate is flat. The substrate may be clear, white, or any color. Generally, the substrate is opaque when dry, so the layers under the substrate are not visible. In many embodiments, the substrate is permanently opaque, even when wet.

Optionally, various fillers or additives may be incorporated into the substrate to control or contribute to the overall color and/or opacity of substrate. Such fillers or additives may include clay, talc, diatomaceous earth, calcium carbonate, calcium sulfate, barium sulfate, iron oxide, titanium oxide, zinc oxide, zinc sulfide, aluminum silicate, organic pigments or a mixture thereof.

Fluid Transportable Ink

Fluid transportable ink is coated onto one surface of the fluid transport substrate to form an ink layer. In embodiments comprising a hydrophilic resin layer, the ink may be coated on the hydrophilic resin layer as depicted in the figures. Ink is defined as a dispersion of a pigment or a dye solution produced as a fluid, paste or a powder. Upon exposure to a fluid, the fluid transportable ink is mobilized and flows with the fluid through the substrate. In some embodiments, a hole in the substrate exposes the ink and assists in the displacement of the ink in the event of fluid exposure.

For example, a water soluble ink is suitable for the present invention. In specific embodiments, the ink may be HP Ink Jet cartridge 51649a printed blue ink, commercially available from Hewlett Packard Co., Boise, Id. Other examples include blue dye powder sold under the tradename HIDACID AZURE Blue dustless 20DA2228 commercially available from B.F. Goodrich, Cincinnati, Ohio and red dyes sold under the tradenames FASTUSOL Red 43LN and BASACID RED NB 391L, both commercially available from BASF Corp. of Mount Olive, N.J.

The ink may be dispersed on the substrate. In other embodiments, the ink is dispersed on the adhesive layer, which is then brought into contact with the substrate. The ink may be dispersed using various coating and printing techniques chosen to be suitable for a particular ink. For example, the ink may be dispersed using an ink jet printer, gravure printing, flexographic printing, letter press printing or powder coating techniques. The ink may be dispersed on the substrate in a variety of coverage, for example a predetermined pattern, a random pattern, or complete coverage.

Adhesive

An adhesive layer is applied, for example coated or laminated, onto the surface of the ink layer. The adhesive may be any adhesive, for example a thermally bondable (hot-melt) adhesive or an ultra-violet activated adhesive. Generally, the adhesive layer is a pressure sensitive adhesive. Pressure sensitive adhesives are generally characterized by their properties. Pressure sensitive adhesives are well known to one of ordinary skill in the art to possess properties including the following: (1) aggressive and permanent tack, (2) adherence to a substrate with no more than finger pressure, (3) sufficient ability to hold onto an adherent, and (4) sufficient cohesive strength to be removed cleanly from the adherent. Many pressure sensitive adhesives must satisfy these properties under an array of different stress rate conditions. Additives may be included in the pressure sensitive adhesive to optimize the characteristics of the pressure sensitive adhesive.

Any suitable pressure sensitive adhesive composition can be used for this invention. Generally, the pressure sensitive adhesive should not interfere with the ability of the ink to transport with a fluid, for example by reacting with a treatment on the substrate. The pressure sensitive adhesive component can be any material that has pressure sensitive adhesive properties. Furthermore, the pressure sensitive adhesive component can be a single pressure sensitive adhesive or the pressure sensitive adhesive can be a combination of two or more pressure sensitive adhesives.

Pressure sensitive adhesives useful in the present invention include, for example, those based on natural rubbers, synthetic rubbers, styrene block copolymers, polyvinyl ethers, poly(meth)acrylates (including both acrylates and methacrylates), polyolefins, and silicones.

The pressure sensitive adhesive may be inherently tacky. If desired, tackifiers may be added to a base material to form the pressure sensitive adhesive. Useful tackifiers include, for example, rosin ester resins, aromatic hydrocarbon resins, aliphatic hydrocarbon resins, and terpene resins. Other materials can be added for special purposes, including, for example, oils, plasticizers, antioxidants, ultraviolet ("UV") stabilizers, hydrogenated butyl rubber, pigments, and curing agents.

In one embodiment, the pressure sensitive adhesive is based on at least one poly(meth)acrylate (e.g. is a (meth) acrylic pressure sensitive adhesive). Poly(meth)acrylic pressure sensitive adhesives are derived from, for example, at least one alkyl (meth)acrylate ester monomer such as, for example, isooctyl acrylate, isononyl acrylate, 2-methyl-butyl acrylate, 2-ethyl-hexyl acrylate and n-butyl acrylate; and at least one optional co-monomer component such as, for example, (meth)acrylic acid, vinyl acetate, N-vinyl pyrrolidone, (meth)acrylamide, a vinyl ester, a fumarate, a styrene macromer, or combinations thereof. Generally, the poly(meth)acrylic pressure sensitive adhesive is derived from between about 0 and about 20 weight percent of acrylic acid and between about 100 and about 80 weight percent of at least one of isooctyl acrylate, 2-ethyl-hexyl acrylate or n-butyl acrylate composition, preferably isooctyl acrylate. A suitable embodiment for the present invention is derived from between about 2 and about 10 weight percent acrylic acid and between about 90 and about 98 weight percent of at least one of isooctyl acrylate, 2-ethyl-hexyl acrylate or n-butyl acrylate composition.

The adhesive layer is applied onto the ink layer using any suitable coating or laminating technique. For example, the adhesive layer may be formed by continuous forming methods, including hot melt coating, drawing or extruding, the adhesive composition from the elongating shear force device (e.g. a draw die, a film die, or a rotary rod die) and subsequently contacting the drawn adhesive composition to a moving web (e.g. plastic) or other suitable substrate. A related continuous forming method involves extruding the adhesive composition and a co-extruded backing material from a film die and cooling the layered product to form an adhesive tape. Other continuous forming methods involve directly contacting the adhesive composition to a rapidly moving web or other suitable preformed substrate. Using this method, the adhesive composition is applied to the moving preformed web using a die having flexible die lips, such as a rotary rod die. The adhesive layer may additionally be formed by any non-continuous coating method.

Alternatively, the adhesive may be prepared by dissolving the components of the adhesive composition in a solvent such as toluene and casting over the substrate.

Transparent Layer

The water indicating adhesive article of the present invention optionally has a transparent layer comprising a transparent film on the fluid transporting substrate. The transparent layer is on the substrate surface opposite the ink layer. The transparent layer may extend beyond the edge of the substrate, or may be the same size as the substrate. Generally such a layer may be waterproof. Such a layer protects the water indicating adhesive article from moisture during human handling and from dew/condensation. Additionally, the additional layer may protect the water indicating adhesive article during prolonged submersion and may extend the life of certain water indicating tapes during humidity aging conditions. In certain embodiments, the transparent layer is printable using a variety of printing techniques, including ink-jet printing, thermal transfer printing and flexographic printing. In addition, the transparent layer may be a multi-layer decorative film such as, for example, those disclosed in U.S. Pat. No. 6,117,530 to Jonza et al.

The transparent layer may have an adhesive layer to adhere the transparent layer to the substrate. Alternatively, the transparent layer may be adhered to the substrate by high temperature lamination, thus eliminating the need for an adhesive layer between the substrate and the transparent layer. The transparent layer serves to protect the adhesive article surface from dirt, debris, and handling contaminants as well as holding the color within the paper when the indicator is immersed in water for long periods. When an adhesive article without a protective film is immersed for long periods of time, one potential problem is that it will bleed out or wash out and start to turn back to the original, non-indicating color (white); thus giving a false reading that it was not exposed to water. Also, depending upon the material of the substrate, an adhesive article without a protective film may begin to disintegrate if immersed for long periods of time. However, an adhesive article with a protective cover film will hold the color change in the paper and will not bleed out or disintegrate after long periods of time immersed. Specific examples of transparent layers suitable for the present invention include UPVC backed tapes, such as those sold under the tradename FM046092 clear polyester label stock, available from Emtech Emulsion Technologies, Medina, Ohio, Scotch Premium Transparent Film Tape 600; polypropylene tapes such as those sold under the tradename Scotch Box Sealing Tape 375 and polyester backed tapes such as those sold under the tradename Scotch Box Sealing Tape 355, or 3M™ Thermal Transfer Imprintable Film Tape 7861; all commercially available from 3M Company of St. Paul, Minn.

Additional Layers

The water indicating tape of the present invention may comprise additional layers. For example, some embodiments comprise an additional fluid transport substrate layer between the adhesive layer and the ink layer. The water indicating tape may also comprise a release liner, such as silicone coated paper or film, adhered to the adhesive until the tape is ready to be adhered to a surface.

If the tape is sold in a roll, it may be beneficial to add a release material (e.g., low adhesion backsize) to the side of the tape opposite the adhesive.

Method of Manufacture

The water indicating adhesive article of the present invention is manufactured generally by coating a fluid transport substrate, either single or multilayer as described, with a fluid transportable ink. In certain embodiments, the fluid transport substrate comprises a porous substrate and a hydrophilic resin layer. The hydrophilic resin layer may be coated on the porous substrate. In some embodiments, the hydrophilic resin layer comprises an additive (e.g. titanium dioxide). Other additional layers may also be coated to form the fluid transport substrate. The substrate may be in the form of a sheet, or may be a long strip suitable for rolling the final product into a roll of tape. The ink may be coated to completely cover the substrate, or may be coated in segments or a design. The ink must be coated so that the ink does not bleed through the substrate. For example, the ink may be coated onto a release liner, and then transferred to the substrate.

Adhesive is then applied to the ink as described above. The substrate and the ink may then be completely coated with the adhesive, or may be coated with segments of adhesive. Such a segmented adhesive may be desirable in embodiments where the substrate may have a coating that may be affected by the adhesive. The adhesive is then covered with a release liner if desired.

In other embodiments, the adhesive can be made into a transfer tape by coating the adhesive composition, either completely or in segments, on a liner, or between two liners, coated with a release coating. If the transfer tape is made by coating between two liners, one of the liners of the transfer tape can be removed to expose the adhesive surface. The adhesive surface may then be applied to the ink layer, or the adhesive surface may be coated with the fluid transportable ink and then laminated to the substrate. The remaining release liner aids in transferring the adhesive to the substrate.

Individual labels may be created by converting the sheets into individual labels, for example by die cutting the sheet. The sheet may be die cut into any size or shape, such as circles or squares. For example, the sheet may be die cut into a circle with a diameter greater than 5 millimeters for ease of handling. Specific examples include rectangles used for an informative label, or small circles placed inside an electronic device.

The optional transparent layer may be laminated or adhered to the substrate prior to converting the substrate into an individual label.

Use of the Adhesive Article

The adhesive article of the present invention may be a roll of tape. The adhesive article may also be an individual label. In these embodiments, the adhesive article is placed on a device, such as a portable electronic device. In some embodiments, the adhesive article is printed, for example the adhesive article could include warranty information in addition to acting as an indicator for fluid exposure.

Upon exposure to a fluid, the adhesive article of the present invention exposes to indicate the fluid contact. Depending on the ink and the substrate used in the adhesive article, the fluid could include polar solvents such as alcohol, non-polar solvents, bodily fluids and water. Generally, the adhesive article can indicate exposure to a fluid if the ink is soluble in the fluid and the fluid transports through the substrate. Specifically, the invention is beneficial to indicate the exposure to fluids containing water, such as consumable alcoholic drinks. At exposure, the fluid transportable ink migrates through the fluid transport substrate to cause a substantial color change on at least a portion of the fluid transport substrate. The substantial color change is defined as, for example white to red.

Objects and advantages of this invention are further illustrated by the following examples. The particular materials and amounts thereof, as well as other conditions and details, recited in these examples should not be used to unduly limit this invention.

EXAMPLES

TABLE 1

Materials:

| Item | Description | Supplier |
|---|---|---|
| Absorbent Substrate A | 3 mil (76 micrometer) GW FORM Bond, cellulose paper | MeadWestvaco Corporation of Wickliffe, Kentucky |
| Absorbent Substrate B | 4 mil (102 micrometer) GW FORM Bond, cellulose paper | MeadWestvaco Corporation of Wickliffe, Kentucky |
| Absorbent Substrate C | 4 mil (102 micrometer) Hammermill CopyPlus Copy Paper, 84 Brightness | International Paper of Memphis, Tennessess |
| PVA #1 | Polyvinyl alcohol; MW 2000 | Sigma-Aldrich Inc. of St. Louis, Missouri |
| PVA #2 | Polyvinyl alcohol; MW 89,000 to 98,000 | Sigma-Aldrich Inc. of St. Louis, Missouri |
| PVP #1 | Polyvinylpyrrolidone; Ave. Molecular Weight 10,000 | Sigma-Aldrich Inc. of St. Louis, Missouri |
| PVP #2 | Polyvinylpyrrolidone; Ave. Molecular Weight 40,000 | Sigma-Aldrich Inc. of St. Louis, Missouri |
| PVP #3 | Polyvinylpyrrolidone; Ave. Molecular Weight 360,000 | Sigma-Aldrich Inc. of St. Louis, Missouri |
| PVP #4 | Polyvinylpyrrolidone; Ave. Molecular Weight 1,300,000 | Sigma-Aldrich Inc. of St. Louis, Missouri |
| AQUAZOL 500 | Polyethyloxazoline MW 500,000 | Polymer Chemistry Innovations of Tucson, Arizona |
| PVP/VA | Polyvinylpyrrolidone/ Vinyl Acetate Copolymer | S-630, GAF Corporation, New York, New York. |

TABLE 1-continued

Materials:

| Item | Description | Supplier |
|---|---|---|
| $TiO_2$ | Titanium (IV) Oxide, rutile | Alfa Aesar of Ward Hill, Massachusetts |
| Red Dye | BASACID RED NB391L | BASF Corp of Mount Olive, New Jersey |
| Transfer Adhesive | 3M Laminating Adhesive 9447 | 3M Company of St. Paul, Minnesota |
| Transparent Protective Film | 0.5 mil (13 micrometer) Clear polyester labelstocklabel stock FM046092 | Emtech Emulsion Technologies, Medina, OH |

APM: Ascorbic acid phosphoric acid magnesium

The following examples describe the making and testing of a water contact indicator. It is understood that in all the examples, the order of the process may be altered to achieve the same final construction of the various embodiments of the present invention.

The following water dispersible solutions were first prepared; all concentrations are weight/weight percent, unless otherwise specified.

TABLE 2

| Coating #1 | 10% PVA #1 | 1% $TiO_2$ | 89% Deionized Water |
| Coating #2 | 5.3% PVP #3 | 1% $TiO_2$ | 93.7% Deionized Water |
| Coating #3 | 10% AQUAZOL 500 | 1% $TiO_2$ | 89% Deionized Water |
| Coating #4 | 10% PVP #1 | 1% $TiO_2$ | 89% Deionized Water |

Examples 1-4

Examples 1-4 were prepared by applying Coatings #1-#4, respectively, to four separate sheets of Absorbent Substrate A by means of a PAMARCO hand proofer, available from Parmarco Technologies, Inc. of Roselle, N.J., using a 200 pyramid coating cylinder. All samples were dried using a hot air gun. Red Dye was applied by the same means as the Coatings #1-#4 to the coated side of all four sheets of Examples 1-4. Transfer Adhesive was laminated to the coated/dyed side of each sheet of Examples 1-4. To the non-coated/dyed side of the Absorbent Substrate was laminated a Transparent Protective Film. Several small circles with a diameter of 14 mm were die cut from the prepared sheets of Examples 1-4 and applied to a polyester holding sheet for indicator testing.

The polyester holding sheet was simply used to keep track of the indicator circles and to simulate a substrate to which the indicator circles would be applied.

Examples 1-4 were tested according to the following procedure, "One Minute Water Contact Test." One drop of tap water was applied to the edge of the circle for one minute to see how well the sample indicated. The more area of the (Example) circle that turns red, and the more intense the resulting red, the better the indication. After one minute, the remaining water is wiped away with a paper towel. The numerical ratings for level of indication ranges from 1 to 5, where 1=no indication or very little indication, 2=poor, 3=fair, 4=good, 5=excellent. Results of the "One Minute Water Contact Test" for Examples 1-4 are provided in TABLE 3.

TABLE 3

| Example No. | Poly Coating | TiO$_2$ | Level of Indication |
| --- | --- | --- | --- |
| Example 1 | 10% PVA #1 | 1% TiO$_2$ | 2 |
| Example 2 | 5.3% PVP #3 | 1% TiO$_2$ | 2 |
| Example 3 | 10% AQUAZOL 500 | 1% TiO$_2$ | 1 |
| Example 4 | 10% PVP #1 | 1% TiO$_2$ | 4 |

Examples 5-11

Additional water dispersible solutions (coatings) were formulated for the preparation of Examples 5-11.

TABLE 4

| Coating #5 | 14% PVP #3 | 14% TiO$_2$ | 72% Deionized Water |
| --- | --- | --- | --- |
| Coating #6 | 20% PVP #1 | 5% TiO$_2$ | 75% Deionized Water |
| Coating #7 | 10% PVP #1 | 10% TiO$_2$ | 80% Deionized Water |
| Coating #8 | 10% PVP #1 | 5% TiO$_2$ | 85% Deionized Water |
| Coating #9 | 15% PVP #1 | 20% TiO$_2$ | 65% Deionized Water |
| Coating #10 | 10% PVP #1 | 20% TiO$_2$ | 70% Deionized Water |
| Coating #11 | 15% PVP #1 | 35% TiO$_2$ | 50% Deionized Water |

Examples 5-11 were prepared using Coatings #5-#11, respectively, coated onto separate pieces of Absorbent Substrate C in the same manner, and equipment as Examples 1-4. Red Dye and Transfer adhesive were also applied to the coated side of Examples #5-#11 in the same manner as Examples 1-4. A Transparent Protective Film was not laminated to the non-coated/dyed side of the Substrate C. Several small circles with a diameter of 14 mm were die cut from the prepared sheets of Examples 5-11 and applied to a polyester holding sheet for indicator testing.

Examples 5-11 were exposed to temperature and humidity conditions of 55° C./95% RH for 7 days. This exposure testing was performed to determine if the samples indicated a false positive for water contact under such extreme conditions of temperature and humidity.

After Examples 5-11 were removed from the temperature/humidity chambers they were allow to equilibrate to room temperature and humidity. None of the examples 5-11 showed a false positive for water contact. All of the examples did show a very slight color indication, but not enough to be considered exposed to liquid water contact.

Additionally, Examples 5-11 were subjected to the "One Minute Water Contact Test;" the results of which are presented in TABLE 5.

TABLE 5

| Example No. | Amount of PVP | TiO$_2$ | Level of Indication |
| --- | --- | --- | --- |
| Example 5 | 14% PVP #3 | 14% TiO$_2$ | 1 |
| Example 6 | 20% PVP #1 | 5% TiO$_2$ | 2 |
| Example 7 | 10% PVP #1 | 10% TiO$_2$ | 2 |
| Example 8 | 10% PVP #1 | 5% TiO$_2$ | 2 |
| Example 9 | 15% PVP #1 | 20% TiO$_2$ | 2/3 |
| Example 10 | 10% PVP #1 | 20% TiO$_2$ | 2 |
| Example 11 | 15% PVP #1 | 35% TiO$_2$ | 4 |

Examples 12-15

Examples 12-15 were all prepared under production line conditions using Absorbent Substrate B. Examples 12 and 14 were coated with Coating #12, which consisted of PVP #1/TiO$_2$/deionized water at concentrations of 15%/35%/50%.

TABLE 6

| Example No. | Absorbent Substrate | Coating | Transparent Protective Film | Red Dye | Transfer Adhesive |
| --- | --- | --- | --- | --- | --- |
| Example 12 | B | Coating #12 | None | Yes | Yes |
| Example 13 | B | No Coating | None | Yes | Yes |
| Example 14 | B | Coating #12 | Yes | Yes | Yes |
| Example 15 | B | No Coating | Yes | Yes | Yes |

Figure 3:
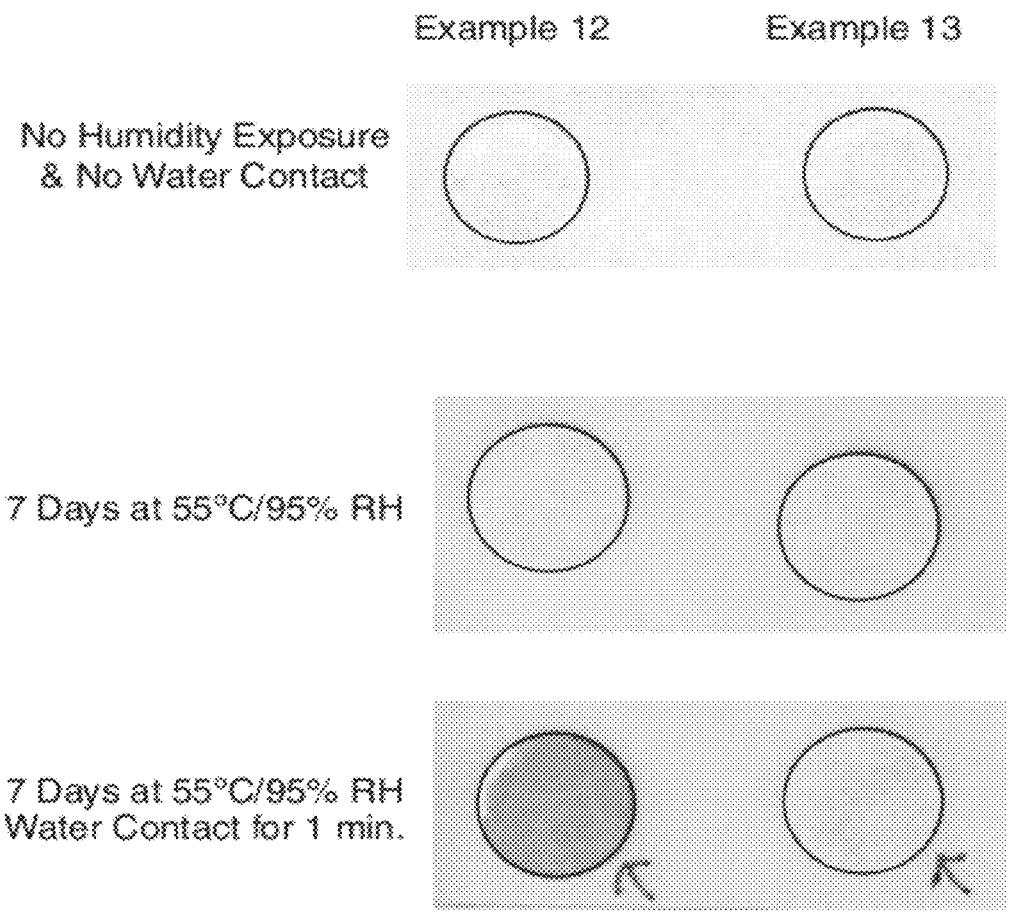
FIG. 3 is a digitally recorded micrograph showing examples after various humidity and water contact exposure as detailed below.

Coating #12 and Red Dye were applied to Absorbent Substrate B using a MarkAndy 4150 Flexographic printing press available from MarkAndy Inc. of St Louis, Mo. Coating #12 was applied using a 300 line Anilox cylinder. The Red Dye was applied to Examples 12-15 with a 360 line anilox cylinder. Transfer Adhesive was laminated to the coated/dyed side of each sheet of Examples 12-15. To the non-coated/dyed side of the Absorbent Substrate B, of Examples 14 and 15 was laminated a Transparent Protective Film. Several small circles with a diameter of 14 mm were die cut from the prepared sheets of Examples 12-15 and applied to a polyester holding sheet for indicator testing. Examples 12-15 were exposed to temperature and humidity conditions of 55° C./95% RH for 7 days. Like Examples 5-11, none of the Examples 12-15 indicated false positives for water contact exposure. Although, all of the Examples 12-15 did show a very slight color indication, but not enough to be considered exposed to water contact. Additionally, after prolonged temperature and humidity exposure, Examples 12-15 were subjected to the "One Minute Water Contact Test." All samples gave a positive water contact indication except Example 13. See FIG. 3 for the appearance of Examples 12 and 13 under various pre-test and post-test conditions.

Examples 16-24

Examples 16-24 were prepared as described for Examples 1-4 with the following modifications. Coating solutions 16-24, shown in TABLE 7, were prepared and applied to Absorbent Substrate C. Results of the "One Minute Water Contact Test" for Examples 16-24 are provided in TABLE 8.

TABLE 7

| Coating #16 | 35% PVP #1 | 0% TiO$_2$ | 65% Deionized Water |
| --- | --- | --- | --- |
| Coating #17 | 15% PVP #1 | 0% TiO$_2$ | 85% Deionized Water |
| Coating #18 | 15% PVP #1 | 35% TiO$_2$ | 50% Deionized Water |
| Coating #19 | 15% PVP #2 | 35% TiO$_2$ | 50% Deionized Water |
| Coating #20 | 15% PVP #3 | 35% TiO$_2$ | 50% Deionized Water |
| Coating #21 | 15% PVP #4 | 35% TiO$_2$ | 50% Deionized Water |
| Coating #22 | 15% PVA #1 | 35% TiO$_2$ | 50% Deionized Water |
| Coating #23 | 15% PVA #2 | 35% TiO$_2$ | 50% Deionized Water |
| Coating #24 | 15% PVP/VA | 35% TiO$_2$ | 50% Deionized Water |

TABLE 8

| Example No. | Poly Coating | TiO$_2$ | Level of Indication |
| --- | --- | --- | --- |
| Example 16 | 35% PVP #1 | 0% TiO$_2$ | 3 |
| Example 17 | 15% PVP #1 | 0% TiO$_2$ | 2 |
| Example 18 | 15% PVP #1 | 35% TiO$_2$ | 2 |
| Example 19 | 15% PVP #2 | 35% TiO$_2$ | 3 |
| Example 20 | 15% PVP #3 | 35% TiO$_2$ | 2 |
| Example 21 | 15% PVP #4 | 35% TiO$_2$ | 2 |
| Example 22 | 15% PVA #1 | 35% TiO$_2$ | 2 |
| Example 23 | 15% PVA #2 | 35% TiO$_2$ | N.D. |
| Example 24 | 15% PVP/VA | 35% TiO$_2$ | 2 |

N.D. - Solution dried out during coating process, unable to obtain sample for testing Examples 25-33

Examples 25-33 were prepared as described for Examples 16-24 above with the following modification. A Transparent Protective Film was not laminated to the non-coated/dyed side of the Substrate C. In this construction, it was possible to coat and dry Example 32 (which corresponds to Example 23 above, but without the protective film) to provide a test sample. Several small circles with a diameter of 14 mm were die cut from the prepared sheets of Examples 25-33 and applied to a polyester holding sheet for indicator testing. Examples 25-33 were then exposed to temperature and humidity conditions as described for Examples 5-11 above. None of the Examples 25-33 showed a false positive for water contact. All of the examples did show a very slight color indication, but not enough to be considered exposed to liquid water contact. The conditioned samples were then subjected to the "One Minute Water Contact Test". The results are presented in TABLE 9.

TABLE 9

| Example No. | Poly Coating | TiO$_2$ | Level of Indication |
|---|---|---|---|
| Example 25 | 35% PVP #1 | 0% TiO$_2$ | 5 |
| Example 26 | 15% PVP #1 | 0% TiO$_2$ | 3 |
| Example 27 | 15% PVP #1 | 35% TiO$_2$ | 4 |
| Example 28 | 15% PVP #2 | 35% TiO$_2$ | 4 |
| Example 29 | 15% PVP #3 | 35% TiO$_2$ | 4 |
| Example 30 | 15% PVP #4 | 35% TiO$_2$ | 3 |
| Example 31 | 15% PVA #1 | 35% TiO$_2$ | 3 |
| Example 32 | 15% PVA #2 | 35% TiO$_2$ | 1 |
| Example 33 | 15% PVP/VA | 35% TiO$_2$ | 4 |

Various modifications and alterations that do not depart from the scope and spirit of this invention will become apparent to those skilled in the art. This invention is not to be unduly limited to the illustrative embodiments set forth herein.

What is claimed is:

1. A fluid contact indicator adhesive article comprising:
    a first layer comprising a fluid transport substrate, the fluid transport substrate comprising a low molecular weight hydrophilic polymer resin layer and a filler to control opacity of the substrate, the first layer having a first major surface that comprises the low molecular weight hydrophilic polymer resin layer and a second major surface;
    a second layer comprising a dry fluid transportable ink disposed upon first major surface of the fluid transport substrate, wherein the fluid transportable ink is capable of migrating through the fluid transport substrate when exposed to fluid, wherein the filler is present in an amount greater than 5 weight percent of the total weight of the polymer resin and filler combined, and wherein the second layer is associated with the hydrophilic polymer resin layer; and
    an adhesive layer associated with the second major surface of the first layer, wherein upon exposure to a fluid, the adhesive article undergoes a substantial color change on at least a portion of the fluid substrate.

2. The adhesive article of claim 1 wherein the color change is from white to red.

3. The adhesive article of claim 1 wherein the fluid transport substrate is a multilayer construction.

4. The adhesive article of claim 1 wherein the low molecular weight hydrophilic polymer resin is a hydrophilic vinyl polymer resin.

5. The adhesive article of claim 4 wherein the hydrophilic vinyl polymer resin comprises polyvinyl pyrrolidone.

6. The adhesive article of claim 1 wherein the low molecular weight hydrophilic polymer resin has a molecular weight of less than 10,000.

7. The adhesive article of claim 1 wherein the filler comprises titanium dioxide.

8. The adhesive article of claim 1 comprising a transparent layer on the first major surface of the first layer.

9. The adhesive article of claim 1 wherein the fluid transport substrate comprises a porous layer.

10. The adhesive article of claim 1 wherein the fluid transport substrate is a cellulose-based paper.

11. The adhesive article of claim 1 wherein the dry fluid transportable ink comprises a water soluble ink.

12. A method of indicating fluid contact, comprising:
    providing the adhesive article comprising:
        a first layer comprising a fluid transport substrate, the fluid transport substrate comprising a low molecular weight hydrophilic polymer resin layer and a filler to control opacity of the substrate, the first layer having a first major surface that comprises the low molecular weight hydrophilic polymer resin layer and a second major surface;
        a second layer comprising a dry fluid transportable ink deposited upon first major surface of the fluid transport substrate, wherein the fluid transportable ink is capable of migrating through the fluid transport substrate when exposed to fluid, wherein the filler is present in an amount greater than 5 weight percent of the total weight of the polymer resin and filler combined, and wherein the second layer is associated with the hydrophilic vinyl polymer resin layer; and
        an adhesive layer associated with the second major surface of the first layer; and
    exposing the adhesive article to a liquid,
    wherein the fluid transportable ink migrates through the fluid transport substrate to cause a substantial color change.

13. The method of claim 12 wherein the adhesive article is exposed to a vapor of the liquid prior to exposure to the liquid.

14. The method of claim 13 wherein the ink migrates through the fluid transport substrate after exposing the adhesive article to the liquid.

15. The method of claim 13 wherein the liquid comprises water.

* * * * *

UNITED STATES PATENT AND TRADEMARK OFFICE
CERTIFICATE OF CORRECTION

PATENT NO. : 8,182,914 B2  
APPLICATION NO. : 12/752314  
DATED : May 22, 2012  
INVENTOR(S) : Paul R LaBrosse Page 1 of 1

It is certified that error appears in the above-identified patent and that said Letters Patent is hereby corrected as shown below:

Column 2,
Line 15, delete "resin layer 22 in" and insert --resin layer 33 is-- therefor.

Column 2,
Line 21, after "ink layer" insert the number --18--.

Column 2,
Line 29, delete "substrate 12." and insert --porous layer 12.-- therefor.

Column 4,
Line 53, delete "poly (meth)acrylates" and insert --poly(meth)acrylates-- therefor.

Column 4,
Line 67, delete "alkyl (meth)acrylate" and insert --alkyl(meth)acrylate-- therefor.

Column 7,
Line 48, delete "Tennessess" and insert --Tennessee-- therefor.

Column 8,
Lines 40-41, delete "Parmarco" and insert --Pamarco-- therefor.

Signed and Sealed this
Eleventh Day of September, 2012

David J. Kappos
*Director of the United States Patent and Trademark Office*